(12) United States Patent
Seltzer et al.

(10) Patent No.: US 10,506,998 B2
(45) Date of Patent: Dec. 17, 2019

(54) AGENT-BASED IMAGING

(75) Inventors: Paul Seltzer, Cleveland, OH (US); Shlomo Gotman, Haifa (IL); Katrina M. Read, Fallston, MD (US); Ekta Dhawal Dharaiya, Twinsburg, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 13/263,856

(22) PCT Filed: Mar. 15, 2010

(86) PCT No.: PCT/IB2010/051102
§ 371 (c)(1),
(2), (4) Date: Oct. 11, 2011

(87) PCT Pub. No.: WO2010/119359
PCT Pub. Date: Oct. 21, 2010

(65) Prior Publication Data
US 2012/0041304 A1 Feb. 16, 2012

Related U.S. Application Data

(60) Provisional application No. 61/174,000, filed on Apr. 30, 2009, provisional application No. 61/170,338, filed on Apr. 17, 2009.

(51) Int. Cl.
*A61B 6/00* (2006.01)
*G16H 40/63* (2018.01)
*A61B 6/03* (2006.01)

(52) U.S. Cl.
CPC .............. *A61B 6/481* (2013.01); *A61B 6/504* (2013.01); *G16H 40/63* (2018.01); *A61B 6/032* (2013.01)

(58) Field of Classification Search
CPC ......... A61B 6/032; A61B 6/481; A61B 6/504; G16H 40/63
See application file for complete search history.

(56) References Cited

U.S. PATENT DOCUMENTS

| | | |
|---|---|---|
| 5,459,769 A | 10/1995 | Brown |
| 5,583,902 A | 12/1996 | Bae |
| 5,687,208 A | 11/1997 | Bae et al. |
| 5,840,026 A | 11/1998 | Uber, III et al. |

(Continued)

FOREIGN PATENT DOCUMENTS

| | | |
|---|---|---|
| CN | 101159185 | 4/2008 |
| JP | 04261279 | 9/1992 |

(Continued)

*Primary Examiner* — Ruth S Smith
(74) *Attorney, Agent, or Firm* — Larry Liberchuk

(57) ABSTRACT

In one embodiment, a method includes correlating, via a data correlator (120), contrast delivery information from an injector (118) for a contrast-enhanced imaging procedure with imaging data acquired by an imaging system (100) utilized for the procedure. In another embodiment, a method includes performing a pre-procedure validation check on at least one of an injector (118) or an imaging system (100) respectively based on at least one protocol parameter of the imaging system (100) or the injector (118) and generating, with the injector (118) or the imagining system (100), a value indicative of the validation check.

31 Claims, 4 Drawing Sheets

(56) References Cited

U.S. PATENT DOCUMENTS

Figure 1:
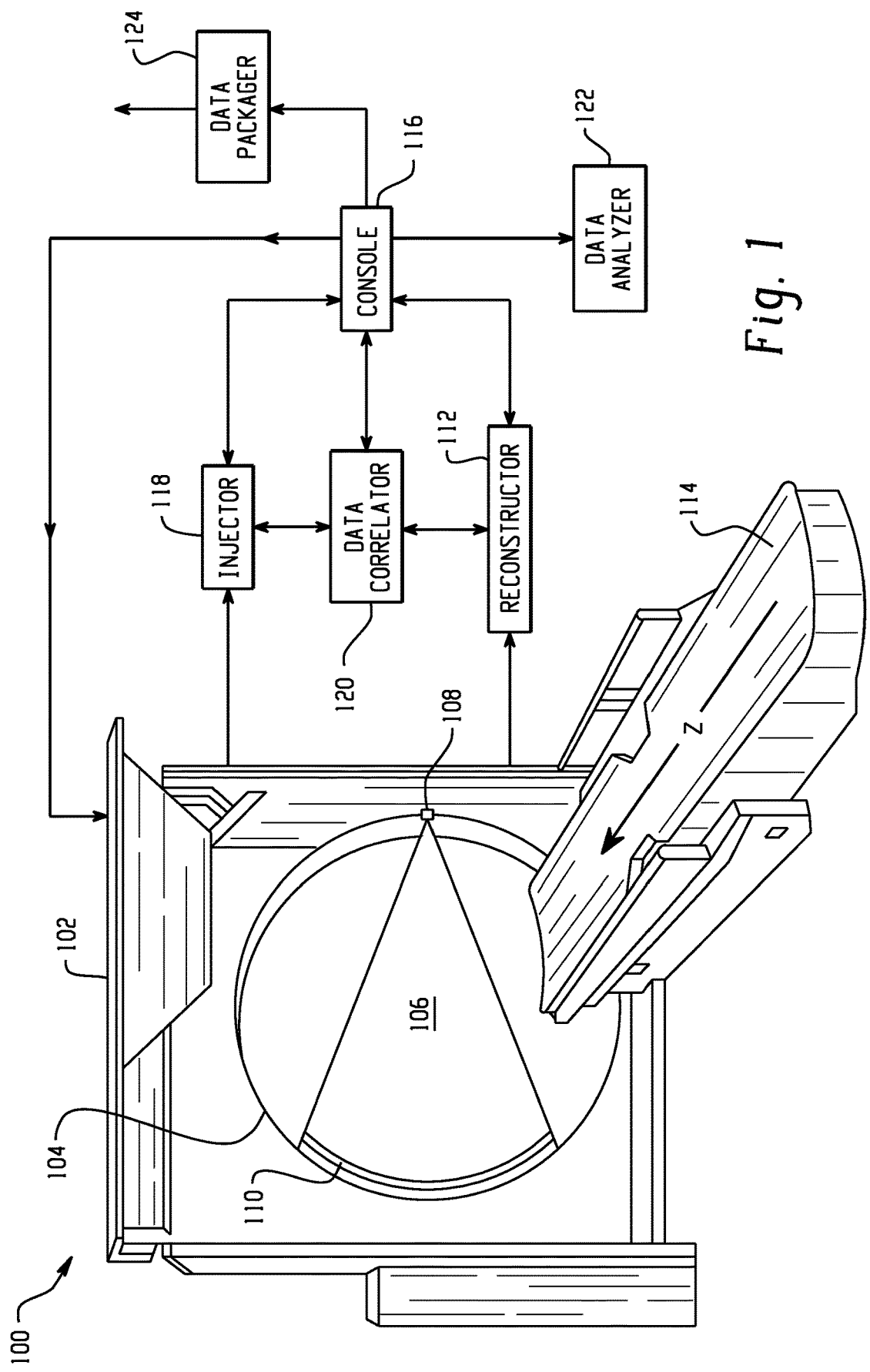

| | | | |
|---|---|---|---|
| 6,397,098 B1 | 5/2002 | Uber | |
| 6,970,735 B2 | 11/2005 | Uber, III et al. | |
| 7,065,395 B2 | 6/2006 | Lienard | |
| 7,280,864 B2 | 10/2007 | Jenkins | |
| 7,327,823 B2 | 2/2008 | Matsuura | |
| 7,974,682 B2 | 7/2011 | Gonzalez | |
| 8,626,342 B2 | 1/2014 | Williams, Jr. et al. | |
| 2002/0165445 A1* | 11/2002 | Uber et al. | 600/407 |
| 2003/0069499 A1 | 4/2003 | Lienard et al. | |
| 2003/0128801 A1 | 7/2003 | Eisenberg et al. | |
| 2006/0030773 A1 | 2/2006 | Uber, III et al. | |
| 2006/0074294 A1 | 4/2006 | Williams, Jr. et al. | |
| 2007/0071299 A1 | 3/2007 | Matsuura | |
| 2008/0119715 A1 | 5/2008 | Gonzalez Molezzi et al. | |
| 2008/0310583 A1 | 12/2008 | Truyen | |
| 2009/0094058 A1* | 4/2009 | Reiner | G06F 19/322 705/3 |
| 2010/0222648 A1* | 9/2010 | Tan | G06F 19/3412 600/301 |
| 2011/0166441 A1* | 7/2011 | Fago | A61M 5/007 600/420 |
| 2013/0102897 A1 | 4/2013 | Kalafut | |
| 2013/0165775 A1* | 6/2013 | Assmann | G06Q 50/24 600/432 |

FOREIGN PATENT DOCUMENTS

| | | |
|---|---|---|
| JP | 2007143880 A | 6/2007 |
| JP | 2009005800 A | 1/2009 |
| JP | 2009045280 | 3/2009 |

\* cited by examiner

AGENT-BASED IMAGING

CROSS REFERENCE TO RELATED APPLICATIONS

This application claims the benefit of U.S. provisional application Ser. No. 61/170,338 filed Apr. 17, 2009 and U.S. provisional application Ser. No. 61/174,000 filed Apr. 30, 2009, both of which are incorporated herein by reference.

The following generally relates to agent-based imaging, and is described with particular application to computed tomography (CT); however, it is also amenable to other imaging modalities.

Imaging procedures, such as an agent-based computed tomography (CT) imaging procedure, often involve intravenous administration of an iodinated contrast or other agent to an object or subject prior to scanning the object or subject. When administering a contrast agent, the agent visually enhances certain anatomical structures of the subject (e.g., blood vessels, etc.) relative to other anatomical structures (e.g., surrounding tissue) in images generated with the data from the scan.

Agents are intravenously administered to the subject through an electronic injector or manually via a syringe and needle by a clinician. With an electronic injector, the clinician loads a syringe filled with the agent into the injector and programs the injector to deliver the agent. Programming includes setting parameters such as delivery rate, delivery volume, delivery sequence (where more than one substance or combination of substances are to be delivered), etc. The injector is then triggered to deliver the agent based on the program.

After a predetermined delay from the administration of the agent to the subject, the subject is scanned. The predetermined delay may depend on various factors such as the delivery point, the region of the subject being scanned, an estimated time to peak contrast enhancement at a region of interest, the time delay between initiating a scan and when scanning begins, etc. One or more images are generated from the scan data. As noted above, when a contrast agent is administered the agent visually enhances certain anatomical structures of the subject in the resulting images.

Unfortunately, the above often relies on the experience of the operator and/or guidelines to determine when to scan the subject after administration of the agent. As such, the expected peak enhancement time for the region being scanned may not correspond to the actual peak enhancement time. As a consequence, the scan may be performed earlier or later than desired, without the operator knowing the scan timing was off, resulting in lower quality images, which could affect diagnosis.

Aspects of the present application address the above-referenced matters and others.

According to one aspect, a method includes correlating, via a data correlator, agent delivery information from an injector for an agent-based imaging procedure with imaging data acquired by an imaging system utilized for the procedure.

In another embodiment, a method includes performing a pre-procedure validation check on at least one of an injector or an imaging system respectively based on at least one protocol parameter of the imaging system or the injector and generating, with the injector or the imagining system, a value indicative of the validation check.

In another embodiment, a system includes a data correlator that correlates agent delivery information from an injector with imaging data acquired by an imaging system.

In another embodiment, a computer readable storage medium containing instructions which, when executed by a computer, cause the computer to perform the acts of: correlating, via a data correlator, agent delivery information from an injector for an agent-based imaging procedure with imaging data acquired by an imaging system utilized for the procedure.

In another embodiment, a method includes generating an image including information from a time-correlated injection of an agent.

The invention may take form in various components and arrangements of components, and in various steps and arrangements of steps. The drawings are only for purposes of illustrating the preferred embodiments and are not to be construed as limiting the invention.

FIG. 1 illustrates an example imaging system in connection with an injector.

Figure 2:
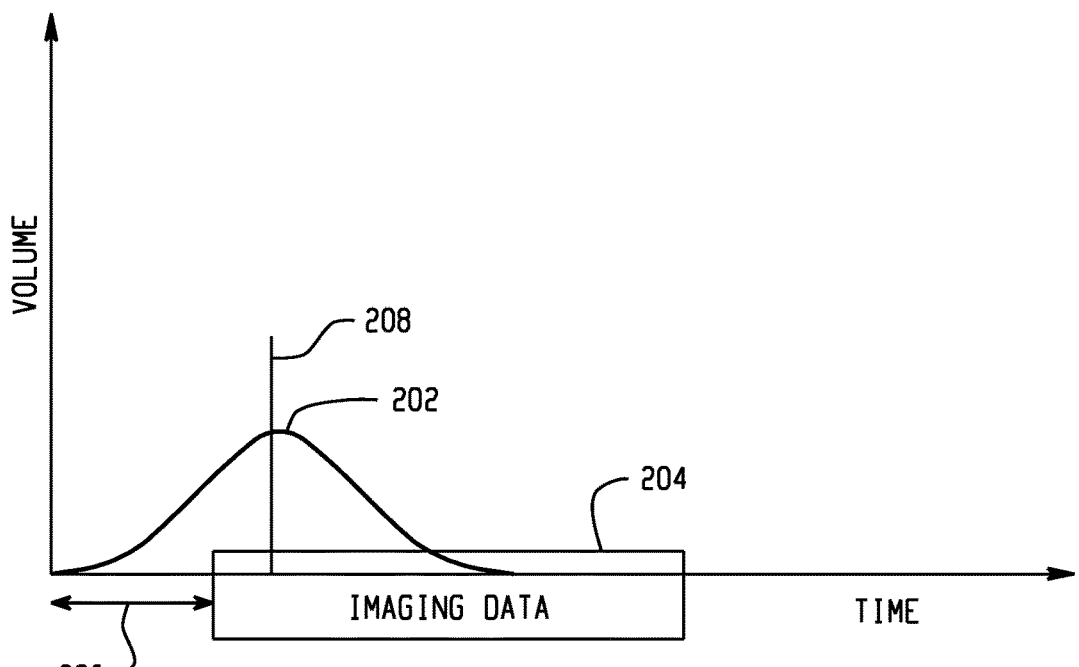

FIG. 2 graphically illustrates correlated injection delivery information and imaging data.

FIGS. 3-7 illustrate various methods.

The following generally relates to correlating imaging data and substance (e.g., agent) delivery information for an imaging procedure. The delivery information can then be used to supplement the imaging data, for example, by providing information that can be used when evaluating images (or projection or image data) generated from the imaging procedure, planning follow up or future similar imaging procedures, optimizing scanning and/or injector parameters, post-validating selected protocols, etc. In addition, communications between the injector used to deliver the substance and the imaging system can be used for pre-scan validation of set up parameters and/or protocols, and/or post-scan validation of the procedure for one or both of the injector or imaging system. Although the embodiments described herein and variants thereof can be used with various imaging modalities such as computer tomography (CT), magnetic resonance (MR), positron emission tomography (PET), combination scanners, etc., for explanatory purposes, the following is described in connection with a CT scanner.

Initially referring to FIG. 1, an imaging system 100, such as a CT scanner, includes a stationary gantry 102 and a rotating gantry 104, which is rotatably supported by the stationary gantry 102 and rotates around an examination region 106 about a z-axis. A radiation source 108, such as an x-ray tube, is supported by the rotating gantry 104. The radiation source 108 emits radiation that traverses the examination region 106. A radiation sensitive detector array 110 subtends an angular arc opposite the radiation source 108 across the examination region 106. The radiation sensitive detector array 110 detects radiation traversing the examination region 106 and generates projection data or a signal indicative thereof.

A reconstructor 112 reconstructs the signal and generates volumetric image data indicative thereof. A patient support 114, such as a couch, supports an object or subject in the examination region 106. A general-purpose computing system serves as an operator console 116. Software resident on the console 116 allows the operator to control the operation of the system 100 such as selecting an imaging protocol such as an agent-based imaging protocol, setting protocol parameters of a device connected to the system 100, initiating scanning, etc. The console 116 includes a communications interface for communicating with one or more devices that may be used in connection with scanning, including receiving information from and/or sending information to a device.

In the illustrated embodiment, an injector 118 is configured to administer one or more substances to the object or subject for a scan. Suitable substances for administration include a contrast agent, saline solution, a combination thereof, a targeted agent, a non-targeted agent, a therapeutic agent, and/or other agent or the like. The illustrated injector 118 may be a single or multi-head injector with one or more bays configured to receive pre-filled and/or fillable containers or syringes. The injector may also include a user interface for programming the injector (e.g., delivery rate, delivery volume, delivery sequence, etc.), starting/stopping administration of the substance, etc., and a pressure sensor for determining delivery pressure. The illustrated injector 118 also includes a communications interface for communicating with one or more devices. Such communication may include sending information such as substance delivery start time, rate and/or volume, substance(s), pressure, stop time, etc.

As noted above, both the console 116 of the system 100 and the injector 118 include communications interfaces. In the illustrated embodiment, the system 100 and the injector 118 are in communication through these interfaces. As described in greater detail below, such interaction may include initiating and performing pre-scan validation checks to verify that the injector 118 can operate in accordance with a selected scan protocol and/or the scanner 100 can operate in accordance with a selected injector protocol. Additionally or alternatively, the interaction between the system 100 and the injector 118 may include one or both of the system 100 or the injector 118 selecting a protocol and/or setting one or more protocol parameters of the other of the injector 118 or the system 100. The pre-scan validation checks also check these parameters and protocols.

By way of non-limiting example, a selected scanner protocol may be based on a particular injector delivery rate, volume or pressure, and the pre-scan check can verify that the injector 118 can deliver at the particular rate, volume or pressure. If it is determined that the injector 118 cannot satisfy the particular delivery rate, volume or pressure, the protocol and/or one or more parameters thereof can be automatically or manually changed, the procedure can be terminated, etc. Otherwise, the procedure can be performed as planned. In another example, a selected injector protocol may be based on a particular scanner ramp up time (time from initiating a scan until x-rays are produced and emitted), and the pre-scan check can verify that the imaging system 100 can satisfy the ramp up time. If not, like above, the protocol and/or one or more parameters thereof can be changed, the procedure can be terminated, etc. Again, the procedure can be performed as planned if the set up is validated by the pre-scan check.

In yet another embodiment, scanner and/or injector protocol validation may also include determining whether a specified and/or recommended protocol can be used with a particular patient to be scanned. Patient information, protocols and/or other information used for such validation can be obtained from a Picture Archiving and Communication System (PACS), a Radiology Information System (RIS), a Hospital Information System (HIS), and/or other local or networked data repository such as a storage, database, and/or archival system. In yet another instance, the information is input or otherwise provided by a user of the system. If the protocol cannot be used, then the protocol and/or one or more parameters thereof can be changed. The patient information can also be used to select a scanner and/or injector protocol for a particular patient.

A data correlator 120 correlates injection delivery information and scanning information. The data correlator 120 is illustrated as a separate component, but can be part of the system 100, such as part of the console 116 or other part of the system 100, or remote from the system 100 such as part of a remote workstation or the like. In one instance, the data correlator 120 correlates injection delivery information and scanning information based on time. For example, the injection delivery information and scanning information can be correlated based on a common time frame of reference.

Various approaches can be used to provide data for correlating the information based on time. For example, in one approach the system clocks of the scanner 100 and the injector 118 are first synchronized with each other. The injector 118 time stamps substance delivery information (e.g., rate, volume, pressure, etc.) and transmits the time stamped data to the data correlator 120. The data correlator 120 correlates the injection information with the imaging information by correlating the time from the time stamps of the injection information with the acquisition time of the projection and/or image data from the scanner 100. Of course, the injector 118 also sends other information to the data correlator 120 such as delivery start and stop time, information indicative of the point of delivery (e.g., arm, leg, etc.), and/or other information.

The above discussed approach can be implemented using Network Time Protocol (NTP) or other protocol, and the transmission of the injection delivery information can be near real-time or real-time (e.g., indicative of state when the information is sent) or delayed, as the information carries the time stamp. In another approach, the clocks of the imaging system 100 and injector 118 are not synchronized. With this approach, the transmission of the injection delivery information from the injector 118 is in near real-time or real-time. For example, in one instance the injector 118 transmits the substance delivery information with a latency of less then a tenth of second from the actual time. Other approaches are also contemplated herein.

A data analyzer 122 is used to analyze the imaging data, including projection data and/or image data. In one instance, this includes analyzing the imaging data in connection with the injection delivery information. In one embodiment, this includes graphically displaying a mapping between the substance delivery information and the imaging data.

By way of non-limiting example, FIG. 2 shows a mapping between delivered volume 202 and data acquisition 204 as a function of time, where the y-axis represents delivered volume and the x-axis represents time. The delay between the start of the delivery of the substance and the start of the scan is shown at 206. Although the delivered volume 202 is represented using a bell shaped profile, it is to be understood that the illustrated profile is for explanatory purposes and is not limiting. In addition, where two or more substances are administered to the subject, the mapping may include multiple profiles. Similar mappings can be generated for delivery rate, pressure, etc.

The illustrated mapping in FIG. 2 allows for determining a value indicative of the volume of the substance for a particular image(s) or data point(s) in the imaging data. For example, in the illustrated embodiment the operator positions a selector 208 over a region of interest in the imaging data, which allows the operator to see the volume of the substance corresponding to that region, along with the distribution of the substance before and during scanning Additionally or alternatively, a value of the volume can be displayed and/or otherwise communicated to the operator and/or system 100. Other information such as the deliver point of the substance may also be provided along with the volume information.

It is to be appreciated that such a mapping can be displayed along with an imaging data viewing window, wherein the selector 208 is automatically positioned along the x-axis based on the data being viewed by the operator. As such, corresponding delivered volume information is dynamically provided to the operator or the system 100 as the operator scrolls or otherwise navigates through the imaging data. Alternatively, the mapping is used to provide the volume information, such as a single or multiple values, without displaying FIG. 2. Other approaches not including the selector 208 are also contemplated herein.

The data analyzer 122 can also perform a post-scan validation of the scanner and/or injector protocol. The post-scan validation can be used to determine whether the selected scanner and/or injector protocol was satisfactory. This may entail determining image quality information from an image such as an average gray scale value for an indentified region of interest and comparing the value with an expected value. The correlation between agent delivery and the imaging data can be used to extract agent delivery information for the image. Such data may be used to determine the expected gray scale value and/or explain a difference between the value and the expected value. If the value satisfies predetermined acceptance criteria, the protocol(s) can be stored and utilized again with the patient and/or used when selecting scanner and/or injector protocol for another patient. If the value is deemed unsatisfactory, the scanner and/or injector protocol can be modified or other protocols can be selected for a follow-up scan or planning a scan for another patient.

A data packager 124 packages the substance delivery information and the scan information. In one instance, this includes packing the information in a Digital Information Imaging and Communications in Medicine (DICOM) or other format. The packaged information may include a time from injection, a time to peak contrast enhancement, delivery rate and/or volume, blood vessel pressure, delivery location, and/or other information for the imaging data, including on an image by image basis. The packaged data can be sent to another scanner, a remote workstation, storage such as a Picture Archiving and Communication System (PACS), a Radiology Information System (RIS), a Hospital Information System (HIS), and/or other storage and/or archival system.

FIGS. 3-7 illustrate various methods. It is to be appreciated that the ordering of the acts in one or more of the methods is for explanatory purposes and is not limiting. In other embodiments, one or more acts can be performed in a different order. Moreover, one or more of the acts may be omitted and/or one or more additional acts may be included.

Figure 3:
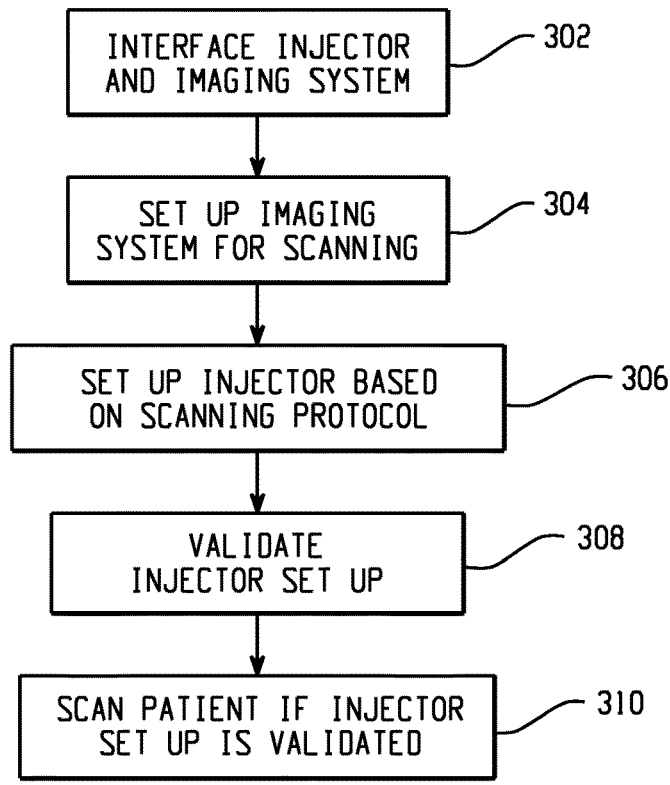

With respect to FIG. 3, at 302 the injector 118 is interfaced with the imaging system 100. At 304, the imaging system 100 is set up for scanning a patient. This may entail selecting a scan protocol and/or setting scan protocol parameters based on the patient, the procedure, and/or otherwise. At 306, the injector 118 is set up to administer a substance(s) to the patient for a scan. This may include programming parameters of the injector 118 such as delivery sequence, delivery rate, delivery volume, etc. based on the selected scanning protocol. Such programming can be performed at the injector 118 or through the console 116.

At 308, a pre-scan validation check is performed on the injector 118. In one instance, this may include determining if the injector 118 is configured to operate based on the selected scan protocol. For example, the scan protocol may be based on a substance delivery rate that may or may not be achievable by the particular injector 118. At 310, if the pre-scan validation check is satisfied, the injector 118 and imaging system 100 can be employed for scanning the object or subject as planned. Otherwise, the imaging system 100 and/or injector 118 set up can be adjusted, the procedure can be cancelled, etc. In one instance, the imaging system 100 and/or injector 118 suggests adjustments.

Figure 4:
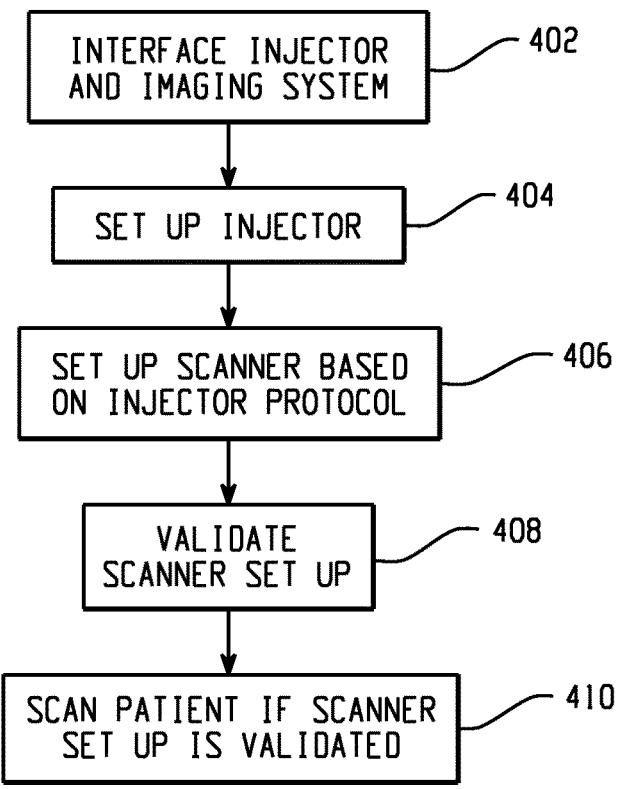

With respect to FIG. 4, at 402 the injector 118 is interfaced with the system 100 as described herein. At 404, the injector 118 is set up to concurrently and/or individually administer one or more substances to a patient for a scan. By way of non-limiting example, the injector 118 may be set up to first administer a contrast agent, then a mixture of a contrast agent and saline, and then just saline At 406, the imaging system 100 is set up for scanning the patient. This may include selecting a scan protocol and/or setting one or more scan protocol parameters based on the injector protocol.

At 408, a pre-scan validation check is performed on the scanner 100. In one instance, this may include determining if the imaging system 100 can operate based on the selected injector protocol. For example, the injector protocol may be based on a scan ramp up time that may or may not be achievable by the imaging system 100. At 410, if the pre-scan validation check is satisfied, the injector 118 and imaging system 100 can be employed for scanning the object or subject as planned. Otherwise, the imaging system 100 and/or injector 118 set up can be adjusted, the procedure can be cancelled, etc. Likewise, in one instance the imaging system 100 and/or injector 118 suggests adjustments.

In another embodiment, pre-scan validation checks can be performed on both the injector 118 and the imaging system 100 as described in connection with FIGS. 3 and 4 and/or otherwise.

Figure 5:
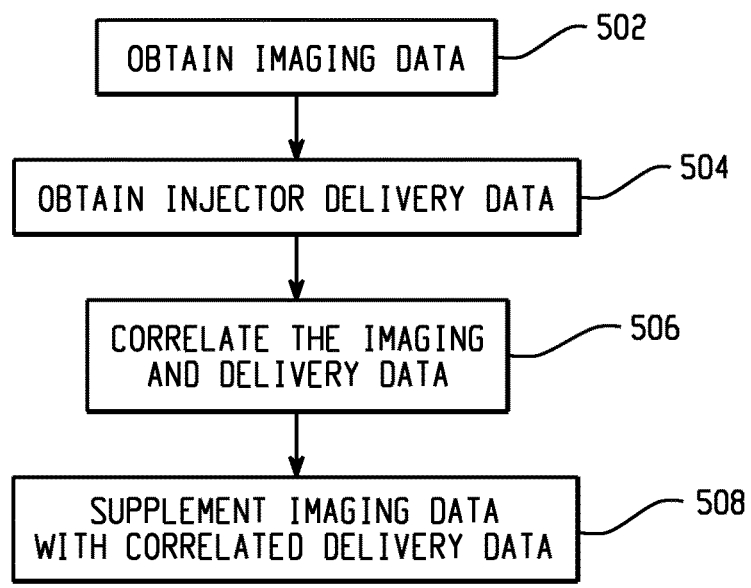

With respect to FIG. 5, at 502 imaging data is obtained for an agent-based imaging procedure. At 504, concurrently acquired agent delivery data is obtained for the imaging procedure. At 506, the imaging data and the agent delivery data are correlated based on a common reference. As described herein, the common reference can be synchronized clocks of the injector 118 and the system 100, the clock of the system 100, and/or other reference.

At 508, the correlated agent delivery data is used to supplement the imaging data. As described herein, this may include using the agent delivery data to facilitate evaluating the image data. For example, where the Hounsfield number in a particular image is outside of an expected range, the correlation can be used to determine contrast delivery characteristics or other image quality information for the image, which may provide some indication such as the data used to reconstruct the image was not acquired at peak contrast enhancement as expected.

The anatomical injection point may also be taken into consideration. Moreover, the correlated information can be used to post-validate one or both of the scanner or injector protocol. As noted above, if one or both of the protocols are deemed unsatisfactory, the scanner and/or injector protocol can be modified or other protocols can be selected for a follow-up scan or for planning a scan for another patient.

Figure 6:
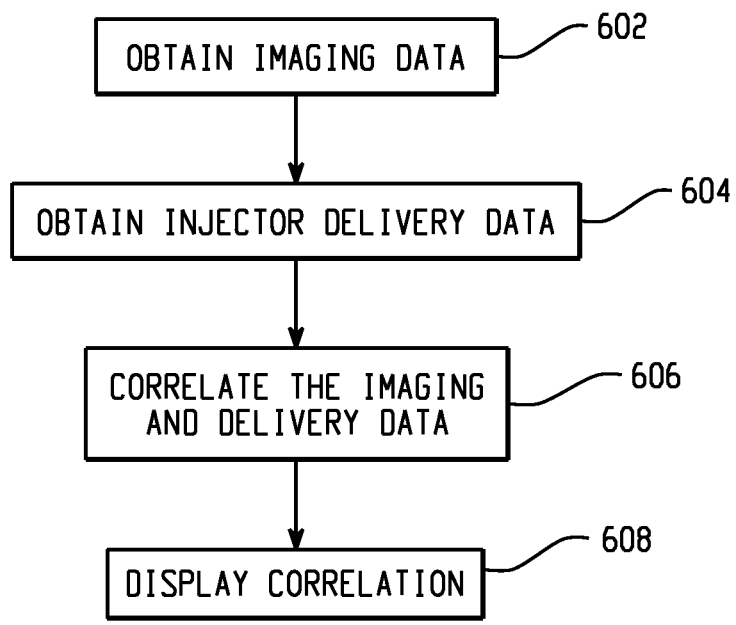

With respect to FIG. 6, at 602 imaging data is obtained for an agent-based imaging procedure. At 604, concurrently acquired contrast delivery data is obtained for the imaging procedure. At 606, the imaging data and the agent delivery data are correlated based on a common reference. As described herein, the common reference can be synchronized clocks of the injector 118 and the system 100, the clock of the system 100, and/or other reference.

At 608, a mapping representing the correlations generated and graphically displayed. In one instance, this includes superimposing a graphical distribution of the agent delivery information and the imaging data as a function of a common time reference. This allows for obtaining contrast delivery information for all or a particular image(s), image data and/or projection data. Alternatively, delivery information for a particular image and/or moment in time can be obtained.

Figure 7:
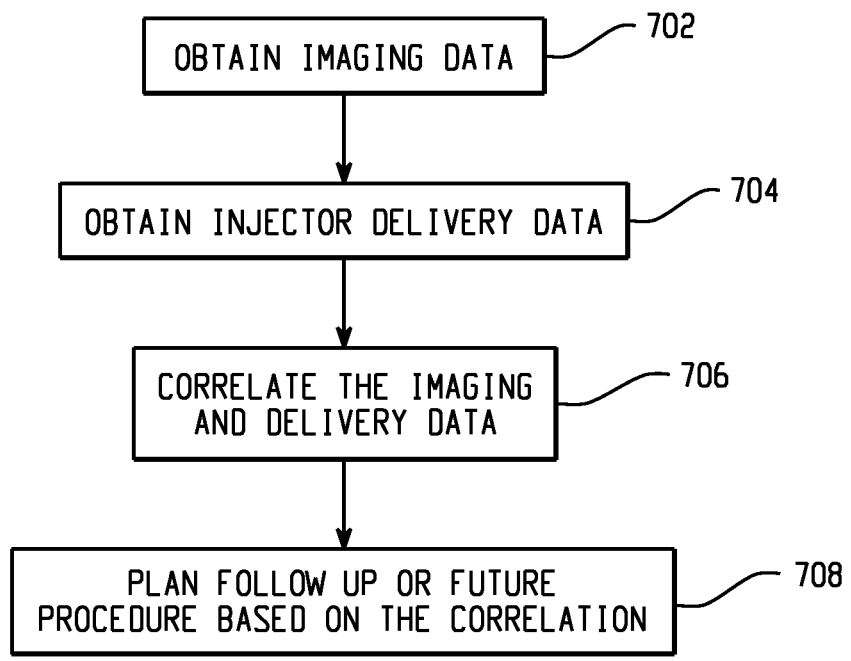

With respect to FIG. 7, at 702 imaging data is obtained for an agent-based imaging procedure. At 704, concurrently acquired agent delivery data is obtained for the imaging procedure. At 706, the imaging data and the agent delivery data are correlated based on a common reference. As described herein, the common reference can be synchronized clocks of the injector 118 and the system 100, the clock of the system 100, and/or other reference.

At 708, the combination of the image data and the agent delivery data is used to plan a follow up and/or future similar procedure. For example, the combination of the data can be used to determine if starting the scan earlier or later from the contrast delivery time would make it more likely to capture peak contrast enhancement of the scanned region of interest. In this instance, a distribution and/or one or more individual values of the contrast delivery information can be used. Other information such as the contrast delivery point can also be employed when planning the follow up and/or future procedure.

The above can be implemented as a console application of a scanner and/or an image processing or planning workstation. By way of example, the above may be implemented by way of computer readable instructions, which when executed by a computer processor(s) (a processor of the console or workstation), cause the processor(s) to carry out the described acts. In such a case, the instructions are stored in a computer readable storage medium associated with or otherwise accessible to the relevant computer.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A method, comprising:
    receiving, by an imaging system, scan parameters for an agent-based imaging procedure from a selected scan protocol for the agent-based imaging procedure,
    wherein the imaging system includes a computed tomography or a positron emission tomography scanner, the scan protocol includes injector delivery parameters for the agent-based imaging procedure, and the injector delivery parameters are selected from a group consisting of: a delivery rate, a delivery volume, or a delivery pressure;
    configuring the imaging system for the agent-based imaging procedure with the scan parameters;
    determining, during a pre-scan validation check of an injector, that the injector is configured to deliver a contrast agent using the injector delivery parameters during the agent-based imaging procedure;
    scanning, in response to determining that the injector is configured to deliver the contrast agent using the injector delivery parameters during the agent-based imaging procedure, a subject with the imaging system during the agent-based imaging procedure, which produces imaging data of the subject for the agent-based imaging procedure;
    receiving, by the imaging system, agent delivery information of an agent delivered to the subject with the injector during the agent-based imaging procedure and sent by the injector to the imaging system;
    correlating, by the imaging system, the agent delivery information with the imaging data as a function of time;
    constructing a graph of the agent delivery information with the image data as a function of the time based on a result of the correlating;
    displaying the graph;
    receiving an input indicating a time point of interest on the graph; and
    displaying the agent delivery information for the time point based on the result of the correlating.

2. The method of claim 1, wherein the agent delivery information and the imaging data are correlated as a function of a common time frame of reference.

3. The method of claim 1, further including synchronizing a first clock of the injector and a second clock of the imaging system, wherein the agent delivery information and the imaging data are correlated based on the synchronized clocks.

4. The method of claim 1, wherein the injector conveys real-time agent delivery information in real-time, and the agent delivery information and the imaging data are correlated based on a single clock.

5. The method of claim 1, furthering including presenting a distribution of the agent delivery information correlated with the imaging data.

6. The method of claim 1, furthering including supplementing the image data with the correlated agent delivery information.

7. The method of claim 1, furthering including:
    adjusting the imaging system in response to determining that the injector is not configured to deliver the contrast agent using the injector delivery parameters during the agent-based imaging procedure.

8. The method of claim 1, wherein the pre-procedure validation check determines if the imaging system is capable of scanning within a scan ramp up time from injection specified by an injector protocol.

9. The method of claim 1, further including:
    performing a pre-procedure validation check of at least one of a selected scan protocol or a select injector protocol based on patient information.

10. The method of claim 9, further comprising:
    canceling the agent-based imaging procedure in response to determining that the injector is not configured to deliver the contrast agent using the injector delivery parameters during the agent-based imaging procedure.

11. The method of claim 1, further including:
    performing a post-procedure validation check of at least one of a scan or an injector protocol based on the correlation and an image quality of the imaging data.

12. A system, comprising:
    a computed tomography or a positron emission tomography imaging system configured to scan an object during an agent-based imaging procedure and based on a scan protocol for the agent-based imaging procedure,
    wherein the scan protocol includes injector delivery parameters for the agent-based imaging procedure, the injector delivery parameters are from a group consisting of: a delivery rate, a delivery volume, or a delivery pressure, and the imaging system is configured to communicate the injector delivery parameters to an injector through complementary communications interfaces of the imaging system and the injector, and wherein the imaging system is configured to determine during a pre-scan validation check of the injector that the injector is configured to deliver a contrast agent using the injector delivery parameters during the agent-based imaging procedure, and, in response to determining during the pre-scan validation check of the injector that the injector is configured to deliver the contrast agent with the injector delivery parameters, scan the object as the contrast agent is delivered by the injector with the injector delivery parameters to produce volumetric image data.

13. The system of claim 12, wherein the imaging system is further configured to correlate agent delivery information with the volumetric imaging data as a function of time, construct a graph of the agent delivery information with the volumetric image data as a function of the time based on a result of the correlating, displays the graph, receive an input indicating a time point of interest on the graph, and display the agent delivery information for the time point based on the result of the correlating.

14. The system of claim 12, wherein the imaging system correlates agent delivery information and the imaging data as a function of a common time frame of reference.

15. The system of claim 12, wherein the imaging system includes a radiation source, a radiation sensitive detector, and a reconstructor to perform the scan.

16. The system of claim 12, wherein the imaging system receives real-time agent delivery information in real-time from the injector, and correlates agent delivery information and the imaging data based on a single clock.

17. The system of claim 12, wherein the imaging system displays a distribution of agent delivery information correlated with the imaging data.

18. The system of claim 12, wherein the imaging system supplements the image data with correlated agent delivery information.

19. The system of claim 12, wherein the imaging system is configured to perform a pre-procedure validation check that determines if the imaging system is capable of scanning within a scan ramp up time from injection by the injector protocol.

20. The system of claim 12, wherein the imaging system is configured to perform a pre-procedure validation check of at least one of a selected scan protocol or a select injector protocol based on patient information.

21. The system of claim 12, wherein the imaging system is configured to perform a post-procedure validation check of at least one of a scan or an injector protocol based on the correlation and an image quality of volumetric image data.

22. A system, comprising:
a computed tomography or a positron emission tomography imaging system configured to scan an object during an agent-based imaging procedure and based on scan parameters from an injector protocol for the agent-based imaging procedure, wherein the injector protocol includes injector delivery parameters for the agent-based imaging procedure, the injector delivery parameters are from a group consisting of: a delivery rate, a delivery volume, or a delivery pressure, and the imaging system is configured to receive the injector delivery parameters from an injector through complementary communications interfaces of the imaging system and the injector, and wherein the imaging system is configured to determine during a pre-scan validation check of the imaging system that the imaging system is configured to operate based on the scan parameters from the injector protocol during the agent-based imaging procedure, and, in response to determining during the pre-scan validation check of the imaging system that the imaging system is configured to operate based on the scan parameters from the injector protocol during the agent-based imaging procedure, scan the object as the contrast agent is delivered by the injector with the injector delivery parameters to produce volumetric image data.

23. The system of claim 22, wherein the imaging system is further configured to correlate agent delivery information with the volumetric imaging data as a function of time, construct a graph of the agent delivery information with the volumetric image data as a function of the time based on a result of the correlating, display the graph, receives an input indicating a time point of interest on the graph, and display the agent delivery information for the time point based on the result of the correlating.

24. The system of claim 22, wherein the imaging system is configured to adjust the injector in response to determining during the pre-scan validation check of the imaging system that the imaging system is not configured to operate based on the scan parameters from the injector protocol during the agent-based imaging procedure.

25. The system of claim 22, wherein the imaging system is configured to cancel the agent-based imaging procedure in response to determining during the pre-scan validation check of the imaging system that the imaging system is not configured to operate based on the scan parameters from the injector protocol during the agent-based imaging procedure.

26. The system of claim 22, wherein the imaging system is configured to adjust the imaging system in response to determining during the pre-scan validation check of the imaging system that the imaging system is not configured to operate based on the scan parameters from the injector protocol during the agent-based imaging procedure.

27. The system of claim 22, wherein the imaging system displays a distribution of agent delivery information correlated with the imaging data.

28. The system of claim 22, wherein the imaging system supplements the image data with correlated agent delivery information.

29. The system of claim 22, wherein the imaging system is configured to perform a pre-procedure validation check that determines if the imaging system is capable of scanning within a scan ramp up time from injection by the injector protocol.

30. The system of claim 22, wherein the imaging system is configured to perform a pre-procedure validation check of at least one of a selected scan protocol or a select injector protocol based on patient information.

31. The system of claim 22, wherein the imaging system is configured to perform a post-procedure validation check of at least one of a scan or an injector protocol based on the correlation and an image quality of volumetric image data.

* * * * *